US008968773B2

(12) United States Patent
Thomas et al.

(10) Patent No.: US 8,968,773 B2
(45) Date of Patent: *Mar. 3, 2015

(54) SILICONE FILM FORMER FOR DELIVERY OF ACTIVES

(75) Inventors: Xavier Thomas, Famars (FR); Virginie Caprasse, Oreye (BE); Eric Jude Joffre, Midland, MI (US); Csilla Kollar, Midland, MI (US); David Clayton Gantner, Midland, MI (US); Victor A. Raul, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 740 days.

This patent is subject to a terminal disclaimer.

(21) Appl. No.: 12/300,875

(22) PCT Filed: May 23, 2007

(86) PCT No.: PCT/US2007/012260
§ 371 (c)(1),
(2), (4) Date: Feb. 18, 2009

(87) PCT Pub. No.: WO2007/139812
PCT Pub. Date: Dec. 6, 2007

(65) Prior Publication Data
US 2009/0258058 A1     Oct. 15, 2009

Related U.S. Application Data

(60) Provisional application No. 60/802,708, filed on May 23, 2006.

(51) Int. Cl.
| | | |
|---|---|---|
| A61K 9/70 | (2006.01) | |
| A01N 25/34 | (2006.01) | |
| A61K 9/14 | (2006.01) | |
| C08L 83/04 | (2006.01) | |
| C08G 77/14 | (2006.01) | |
| C08G 77/388 | (2006.01) | |
| C08L 83/06 | (2006.01) | |
| C08K 5/55 | (2006.01) | |
| C08L 83/08 | (2006.01) | |

(52) U.S. Cl.
CPC ............. *A61K 9/7015* (2013.01); *A61K 9/7069* (2013.01); *C08G 77/14* (2013.01); *C08G 77/388* (2013.01); *C08L 83/06* (2013.01); *C08K 5/55* (2013.01); *C08L 83/08* (2013.01)
USPC ........... 424/449; 424/404; 424/488; 524/588; 525/474

(58) Field of Classification Search
None
See application file for complete search history.

(56) References Cited

U.S. PATENT DOCUMENTS

| | | | |
|---|---|---|---|
| 2,676,182 A | 4/1954 | Daudt et al. | ................ 260/448.2 |
| 2,857,356 A | 10/1958 | Goodwin | ......................... 260/42 |
| 3,159,601 A | 12/1964 | Ashby | |
| 3,220,972 A | 11/1965 | Lamoreaux | |
| 3,296,291 A | 1/1967 | Chalk | |
| 3,389,160 A | 6/1968 | Reid | |
| 3,419,593 A | 12/1968 | Willing | |
| 3,445,420 A | 5/1969 | Kookootsedes et al. | |
| 3,516,946 A | 6/1970 | Modic et al. | |
| 3,814,730 A | 6/1974 | Karstedt | |
| 3,936,582 A | 2/1976 | Keiser | ........................... 428/447 |
| 3,989,667 A | 11/1976 | Lee et al. | |
| 3,989,668 A | 11/1976 | Lee et al. | |
| 4,263,274 A | 4/1981 | Kulkarni | |
| 4,269,603 A | 5/1981 | Worth | |
| 4,310,469 A | 1/1982 | Crivello | |
| 4,313,988 A | 2/1982 | Koshar et al. | |
| 4,370,358 A | 1/1983 | Hayes et al. | |
| 4,501,861 A | 2/1985 | Woodbrey | |
| 4,558,110 A | 12/1985 | Lee | |
| 4,584,355 A | 4/1986 | Blizzard | |

(Continued)

FOREIGN PATENT DOCUMENTS

| | | | |
|---|---|---|---|
| CA | 711756 | 6/1965 | |
| CN | 1357022 | 7/2002 | |
| DE | 19918627 | 10/2000 | |
| EP | 0180377 | 5/1986 | ............ A61M 37/00 |
| EP | 0363252 | 4/1990 | |
| EP | 0438496 | 7/1991 | .............. A61L 15/00 |
| EP | 0444921 | 9/1991 | |
| EP | 0465744 | 1/1992 | ................ A61K 9/22 |
| EP | 0506241 | 9/1992 | ................. C08J 9/02 |
| EP | 0572416 | 9/1992 | |

(Continued)

OTHER PUBLICATIONS

Chinese Office Action dated Sep. 9, 2010 pertaining to related Chinese application for Invention No. 200780023995.1.

(Continued)

*Primary Examiner* — Jeffrey T Palenik
(74) *Attorney, Agent, or Firm* — Nixon Peabody LLP (57) ABSTRACT

The invention provides: a cross-linkable therapeutic composition comprising a) a saccharide-siloxane copolymer; b) a crosslinking agent; c) one or more active/inactive ingredients; and d) optionally, a solvent, or solvent mixture, wherein the saccharide-siloxane copolymer has the following formula: $R_2aR_1(3\text{-}a)SiO\text{—}[(SiR_2R_1O)m\text{-}(SiR_12O)n]y\text{-}SiR_1(3\text{-}a)R_2a$ that is further formulaically defined and wherein the saccharide-siloxane copolymer is a reaction product of a functionalized organosiloxane polymer and at least one hydroxy-functional saccharide such that the organosiloxane component is covalently linked via a linking group to the saccharide component; films; and methods related thereto. The composition has therapeutic properties. The invention also provides articles of manufacture including topical and transdermal agent delivery patches comprising the novel film-forming composition and/or films.

15 Claims, 1 Drawing Sheet

(56) References Cited

U.S. PATENT DOCUMENTS

| | | |
|---|---|---|
| 4,584,361 A | 4/1986 | Janik |
| 4,585,836 A | 4/1986 | Homan |
| 4,591,622 A | 5/1986 | Blizzard |
| 4,591,652 A | 5/1986 | DePasquale et al. |
| 4,604,442 A | 8/1986 | Rich |
| 4,631,329 A | 12/1986 | Gornowicz |
| 4,707,531 A | 11/1987 | Shirahata |
| 4,760,025 A | 7/1988 | Estell et al. |
| 4,766,176 A | 8/1988 | Lee |
| 4,774,281 A | 9/1988 | Chaffee et al. |
| 4,784,879 A | 11/1988 | Lee et al. |
| 4,793,555 A | 12/1988 | Lee et al. |
| RE33,141 E | 1/1990 | Gornowicz et al. |
| 4,910,015 A | 3/1990 | Sung et al. |
| 4,939,128 A | 7/1990 | Kato et al. |
| 4,962,076 A | 10/1990 | Chu et al. |
| 4,999,437 A | 3/1991 | Dobler et al. |
| 5,004,791 A | 4/1991 | Billmers |
| 5,011,870 A | 4/1991 | Peterson |
| 5,015,700 A | 5/1991 | Herzig et al. |
| 5,017,654 A | 5/1991 | Togashi et al. |
| 5,036,117 A | 7/1991 | Chung et al. |
| 5,051,455 A | 9/1991 | Chu et al. |
| 5,053,442 A | 10/1991 | Chu et al. |
| 5,075,038 A | 12/1991 | Cole et al. |
| 5,175,325 A | 12/1992 | Brown et al. |
| 5,227,093 A | 7/1993 | Cole et al. |
| 5,252,233 A | 10/1993 | Czech |
| RE34,606 E | 5/1994 | Estell et al. |
| 5,310,843 A | 5/1994 | Morita |
| 5,352,724 A | 10/1994 | Fujiki et al. |
| 5,380,527 A | 1/1995 | Legrow et al. |
| 5,493,041 A | 2/1996 | Biggs et al. |
| 5,654,362 A | 8/1997 | Schulz, Jr. et al. ............ 524/862 |
| 5,665,155 A | 9/1997 | Hohner et al. |
| 5,677,163 A | 10/1997 | Mainzer et al. |
| 5,700,676 A | 12/1997 | Bott et al. |
| 5,750,123 A | 5/1998 | Znaiden et al. |
| 5,831,080 A | 11/1998 | Sejpka et al. |
| 5,891,977 A | 4/1999 | Dietz et al. |
| 5,895,794 A | 4/1999 | Berg et al. |
| 5,972,682 A | 10/1999 | Bott et al. |
| 5,981,680 A | 11/1999 | Petroff et al. |
| 5,990,069 A | 11/1999 | Andre et al. |
| 6,051,216 A | 4/2000 | Barr et al. |
| 6,066,727 A | 5/2000 | Yamamoto et al. |
| 6,132,822 A | 10/2000 | Overcash et al. |
| 6,136,758 A | 10/2000 | Yamada et al. |
| 6,146,664 A | 11/2000 | Siddiqui |
| 6,218,560 B1 | 4/2001 | Abele et al. |
| 6,221,979 B1 | 4/2001 | Lin et al. ...................... 525/477 |
| 6,239,194 B1 | 5/2001 | Standke et al. |
| 6,255,429 B1 | 7/2001 | Griffin et al. |
| 6,325,990 B1 | 12/2001 | Laurent ........................... 424/45 |
| 6,361,716 B1 | 3/2002 | Kleyer et al. |
| 6,372,833 B1 | 4/2002 | Chen et al. |
| 6,398,911 B1 | 6/2002 | Schroeder et al. |
| 6,414,139 B1 | 7/2002 | Unger et al. |
| 6,433,055 B1 | 8/2002 | Kleyer et al. |
| 6,448,329 B1 | 9/2002 | Hirschi et al. |
| 6,465,550 B1 | 10/2002 | Kleyer et al. |
| 6,471,952 B1 | 10/2002 | Dubief et al. |
| 6,471,985 B2 | 10/2002 | Guyuron et al. .............. 424/445 |
| 6,482,969 B1 | 11/2002 | Helmrick et al. |
| 6,500,883 B1 | 12/2002 | Mack et al. |
| 6,517,933 B1 | 2/2003 | Soane et al. |
| 6,534,581 B1 | 3/2003 | Kleyer et al. |
| 6,762,289 B1 | 7/2004 | O'Lenick, Jr. et al. |
| 6,783,692 B2 | 8/2004 | Bhagwagar |
| 6,791,839 B2 | 9/2004 | Bhagwagar |
| 6,815,486 B2 | 11/2004 | Bhagwagar et al. |
| 7,005,281 B2 | 2/2006 | Ohrlein et al. |
| 7,074,490 B2 | 7/2006 | Feng et al. |
| 7,199,205 B2 | 4/2007 | Okawa et al. |
| 7,205,373 B2 | 4/2007 | Brandstadt et al. |
| 7,208,561 B2 | 4/2007 | Yoshitake et al. |
| 7,354,982 B2 | 4/2008 | Yoshitake et al. |
| 7,649,087 B2 | 1/2010 | Yoshitake et al. |
| 7,741,253 B2 | 6/2010 | Hanes |
| 7,834,087 B2 | 11/2010 | Joffre et al. |
| 7,871,987 B2 | 1/2011 | McSuliffe et al. |
| 2001/0021387 A1 | 9/2001 | Krammer et al. |
| 2001/0053897 A1 | 12/2001 | Frate et al. |
| 2003/0180281 A1 | 9/2003 | Bott et al. |
| 2003/0202948 A1 | 10/2003 | Koini et al. |
| 2004/0071746 A1 | 4/2004 | Popplewell et al. |
| 2004/0077816 A1 | 4/2004 | Brandstadt et al. |
| 2004/0082024 A1 | 4/2004 | Brandstadt et al. |
| 2004/0091541 A1 | 5/2004 | Unger ............................ 424/486 |
| 2004/0091730 A1 | 5/2004 | Hart et al. |
| 2004/0221397 A1 | 11/2004 | Trinh et al. |
| 2004/0241130 A1 | 12/2004 | Tamareselvy et al. |
| 2004/0247552 A1 | 12/2004 | Blin et al. .................. 424/70.13 |
| 2004/0254275 A1 | 12/2004 | Fukui et al. |
| 2005/0043365 A1 | 2/2005 | Yoshitake et al. |
| 2006/0013791 A1 | 1/2006 | Shimizu et al. ............. 424/70.12 |
| 2006/0216259 A1 | 9/2006 | Haubennestel |
| 2008/0138386 A1* | 6/2008 | Joffre et al. ................... 424/445 |
| 2008/0199417 A1 | 8/2008 | Joffre et al. |
| 2008/0200612 A1 | 8/2008 | Joffre et al. |
| 2008/0209645 A1 | 9/2008 | Carrillo et al. |
| 2010/0105582 A1 | 4/2010 | Joffre et al. |

FOREIGN PATENT DOCUMENTS

| | | | |
|---|---|---|---|
| EP | 0698633 | 2/1996 | |
| EP | 0848029 | 6/1998 | ............. C08G 77/38 |
| EP | 0865787 | 9/1998 | ............... A61K 9/70 |
| EP | 0869142 | 10/1998 | ............. C08G 77/50 |
| EP | 0874017 | 10/1998 | |
| EP | 0934959 | 8/1999 | ........... C08G 283/12 |
| EP | 0962482 | 12/1999 | |
| EP | 1020494 | 2/2000 | |
| EP | 1057872 | 12/2000 | ............. C08L 83/14 |
| GB | 2407496 | 5/2005 | ............... A61K 9/70 |
| JP | 62-68820 | 3/1987 | ............. C08G 77/40 |
| JP | 62-68820 | 4/1987 | |
| JP | 63 139106 | 6/1988 | |
| JP | 63-139106 | 6/1988 | ................ A61K 7/00 |
| JP | 05112437 | 5/1993 | |
| JP | 5-186596 | 7/1993 | |
| JP | 5-331291 | 12/1993 | |
| JP | 06-009876 | 1/1994 | ............. C08L 83/08 |
| JP | 7-070204 | 3/1995 | |
| JP | 7-133352 | 5/1995 | ........... C08G 77/452 |
| JP | 8-134103 | 5/1996 | |
| JP | 8-269204 | 10/1996 | ............. C08G 77/42 |
| JP | 9-136901 | 5/1997 | |
| JP | 10-298288 | 11/1998 | |
| JP | 11-92490 | 4/1999 | |
| JP | 11-343347 | 12/1999 | |
| JP | 11-349601 | 12/1999 | |
| JP | 2000-256613 | 9/2000 | ........... C09D 151/02 |
| JP | 2001-524983 | 12/2001 | ........... A61K 9/1270 |
| JP | 2002-146025 | 5/2002 | |
| JP | 2003-503520 | 1/2003 | ............. C08G 77/04 |
| JP | 2003-86233 | 3/2003 | |
| JP | 2004-256539 | 9/2004 | ................ A61K 7/48 |
| JP | 2006-028177 | 2/2006 | ................ A61K 8/72 |
| JP | 2008-525598 | 7/2008 | ............. C08L 83/04 |
| JP | 2008-545838 | 12/2008 | ............. C08G 77/38 |
| WO | WO 90/03809 A1 | 4/1990 | ............. A61L 15/00 |
| WO | WO 92/14428 | 9/1992 | ............. A61L 13/00 |
| WO | EP 0347895 | 11/1993 | |
| WO | WO 94-29322 | 12/1994 | |
| WO | WO 94-29324 | 12/1994 | |
| WO | WO 96-18729 | 6/1996 | |
| WO | EP 0562922 | 5/1997 | |
| WO | WO 97/17057 | 5/1997 | ................ A61L 7/48 |
| WO | WO 97/17058 | 5/1997 | ................ A61L 7/48 |
| WO | WO 97/17059 | 5/1997 | ................ A61L 7/48 |
| WO | WO00/02535 | 1/2000 | |
| WO | WO 00-78844 | 12/2000 | |
| WO | WO01/30784 | 5/2001 | |

(56) References Cited

FOREIGN PATENT DOCUMENTS

| | | | |
|---|---|---|---|
| WO | WO 01/96450 | 12/2001 | ............... C08J 5/00 |
| WO | WO 03-042283 | 5/2003 | |
| WO | WO 03/050144 | 6/2003 | |
| WO | WO 2004-016626 | 2/2004 | |
| WO | WO 2004/024799 | 3/2004 | |
| WO | WO 2004/108175 | 12/2004 | ............. A61L 15/22 |
| WO | WO 2005-047378 | 5/2005 | |
| WO | WO 2005-063855 | 7/2005 | |
| WO | WO 2006-025552 | 3/2006 | |
| WO | WO 2006-064928 | 6/2006 | |
| WO | WO 2006-065282 | 6/2006 | |
| WO | WO 2006-066227 | 6/2006 | |
| WO | WO 2006-071772 | 7/2006 | |
| WO | WO 2006-107003 | 10/2006 | |
| WO | WO 2006-107004 | 10/2006 | |
| WO | WO 2006-127882 | 11/2006 | |
| WO | WO 2006-127883 | 11/2006 | |
| WO | EP 1331248 | 7/2007 | |
| WO | WO 2008-103219 | 8/2008 | |
| WO | WO 2009-125126 | 10/2009 | |

OTHER PUBLICATIONS

Written Opinion of the International Searching Authority corresponding to International Patent Application No. PCT/US2007/12260, European Patent Office, dated Jan. 29, 2008, 5 pages.

International Search Report corresponding to International Patent Application No. PCT/US2007/12260, European Patent Office, dated Jan. 29, 2008, 1 page.

Akimoto, T. et al. Macromol. Chem. Phys. 2000, 201, 2729-2734.

Database WPI Derwent Publications Ltd., London, GB; AN 1988-201757 (XP002395828).

Gupta et al. Biotechnol. Appl. Biochem. (2003) 37: 63-71.

Wagner et al. "Silicon-Modified Carbohydrates Surfactants III: Cationic and Anionic Compounds" Applied Organometallic Chemistry (1997) vol. 11, pp. 523-538.

Simionescu, Bogdan C., Valeria Harabagiu and Cristofor I. Simionescu, "Siloxane-Containing Polymers" in The Polymeric Materials Encyclopedia, CRC Press, Inc., 1996.

Hardman, Bruce, Arnold Torkelson, "Silicones" in Encyclopedia of Polymer Science and Engineering, Edited by H.F. Mark, et.al., 1989, p. 243, vol. 15.

Bishop Determination of the mode and efficacy of the cross linking of guar by borate; dated Mar. 21, 2012; 1 page.

Extended European Search Report PCT/US2007-012260; dated Mar. 21, 2012; 7 pages.

* cited by examiner

SILICONE FILM FORMER FOR DELIVERY OF ACTIVES

CROSS-REFERENCE TO RELATED APPLICATIONS

This application is a U.S. national phase of International Application No. PCT/US2007/012260, filed May 23, 2007, which claims the benefit of priority of U.S. Provisional Application No. 60/802,708, filed on May 23, 2006, both of which are incorporated by reference in their entireties.

FIELD OF THE INVENTION

The present invention relates to the use of saccharide siloxane copolymer compositions that rapidly cure for forming films and delivering actives in personal and healthcare applications.

BACKGROUND OF THE INVENTION

The compositions comprise a single or a blend of saccharide siloxane copolymers that is cross-linked in the presence of reactive cross-linking agents. A preferred saccharide siloxane composition for use in the present invention is a saccharide-derived polyhydroxyl-functional moiety covalently linked to an organosilicon backbone. The cross-linking is achieved by reacting suitable reactive cross-linkers to the copolymers via the polyhydroxy-functionality of the saccharide components.

These film-forming compositions can be used to form a cohesive and substantive films on human or animal biological tissues. The resulting film is designed to deliver actives to the adhering substrate and to the underlying layers. It can also be a protective and barrier film for the covered area, and be used to modify the hydration of the underlying tissues. It can also provide an aesthetic and cosmetic aspect to the covered surface. Thus, it has utility in topical administration, wound care and skin care applications. The invention further relates to the film forming compositions, cured films, and articles of manufacture comprised thereof.

Many formulations for forming films are known in the cosmetic, medical and pharmaceutical art. These include, for example, ointments, salves, creams, lotions, gels, elastomers and the like. Some of these formulations use silicone-based materials as key components. Silicone based materials are desirable in these formulations since they are generally inert to the body. These products are designed to provide a variety of benefits, for example, moisturize dry skin, mask surface imperfections, allow effective delivery of actives while being cosmetically acceptable during and after application onto various skin areas of the body.

Well-known formulations are based on blends of silicone fluids and are broadly used in cosmetic skin care. They combine various viscosities of silicone fluids from volatiles to gum type materials as described in U.S. Pat. No. 6,325,990. Other formulations contain cross-linked organosiloxanes swollen in low molecular weight silicone fluids, and are referred to as elastomer blends as described in U.S. Pat. Nos. 5,654,362 and 6,221,979, and in European Publication Nos: EP848029, EP869142, EP934959, EP1020494, and EP1057872. These compositions show interesting film forming property by spreading easily to various surfaces but their substantivity is low due to an intrinsic cohesion weakness.

Similar compositions, as described for example in WO 97/17057, WO 97/17058, and WO 97/17059, are obtained by blending silicate resins, such as those described in U.S. Pat. Nos. 3,936,582, 2,676,182, 2,857,356 and 2,676,182, with silicone fluids. These compositions show interesting film forming property by spreading easily to various surfaces but their substantivity is limited due to lack of condensation between the resin and the polymeric fluid.

The silicate resin and the silicone fluid can be condensed together according to Canadian Application No. 711,756. The resulting material most likely has adhesive pressure sensitive properties as described in Handbook of Pressure Sensitive Adhesive Technology, $3^{rd}$ edition by Donatas Satas, Satas & Associates, Warwick, R.I. 1989 (ISBN #0963799339), and EP 0180377. These compositions show interesting film forming properties as well as high substantivity and basically demonstrate no tack (essentially, resistance to separation, or, generally, "stickiness") property at high resin content (defined as greater than about 65 weight percent); however because of their intrinsic visco-elastic property they remain sensitive to plasticizing effects and may become tackier by absorbing plasticizing species.

Another example of silicon-based materials in known film forming formulations is provided in European Publication 465,744. This publication teaches the use of a multi-part formulation including an active agent, a Si—H containing polymer, a polymer having unsaturated groups bound to silicon, a catalyst and a hydrophilic component. The formulation is mixed and applied to the body where it cures and forms a controlled release gel. This cross-linkable and elastomeric composition allows for significant reduction of sensitivity to plasticizing effect. The prior art methods such as those described in EP 465,744, however, have several disadvantages. For instance, in such methods the person utilizing the formulation must be skilled so as to ensure adequate mixing of the appropriate amounts of component materials in the formulation. Special care must be exercised to apply the correct amount of the mixed formulation to the desired site before it gels. Similarly, such a method can be an inconvenient and messy for the end user. Similar systems are described in the following publications U.S. Pat. No. 6,471,985, EP 0 506 241, EP 0 865 787, and WO 2004/108175.

Another patent document, WO 90/03809, teaches a coating material for forming bandages comprising a siloxane-containing bandage material diluted in a volatile polydimethylsiloxane. These coatings are distinguishable from the films described and claimed herein. Similar systems are described in the following publications EP 0438496, EP0572416, however these patents describe polymers with acrylate backbones and pendant siloxane functionality.

GB 2407496 and WO 01/96450 teach a method for forming a film on a biological surface. The method comprises mixing an alkylene trialkoxysilyl-terminated polysiloxane; an alkoxysilane; a titanate catalyst; a filler; and a volatile diluent to form a formulation. The formulation is then applied onto a biological surface where it cures in situ on the surface to form a film. This film-former suffers from the characteristic that it cures upon contact with moisture, making it very sensitive to humidity and impacting its stability if it is not properly packaged.

Other known options include solutions of nitrocellulose-silicone blends or silicone-polyamide compositions. While the methods described above may allow for delivering certain important properties, none of them have demonstrated the capability to deliver all important properties in a single embodiment.

Organosiloxane-based elastomers formed from crosslinking organosiloxane polymers are well known in the art and such materials have wide-ranging utility as coatings which confer desirable surface properties to the coated substrate.

Such properties include, for example, enhanced resistance to wear, thermal stability, hydrophobicity and resistance to water, adhesion control and release, frictional control including anti-slip capability, and the like. Various fillers and other additives may be included within the elastomeric matrix to provide coatings with even more varied performance benefits. The mechanical, chemical and ionic characteristics of the crosslinked network matrix influences both the nature and amount of additives that may suitably be included.

Compositions and cured coating compositions comprising crosslinked carbohydrates are known in the art. However, the present inventors are unaware of film-forming compositions comprising saccharide-siloxane copolymers crosslinked via the polyhydroxyl functionality of the saccharide. The networked matrix and cured films formed from these unique crosslinkable compositions provide a blended property profile comprising attributes of both silicone and carbohydrate-based matrices which may support, retain and/or controllably release a variety of additives. Crosslinking via the saccharide component of the copolymer yields elastomers possessing a property profile making them desirable for particular applications.

There is a need in the art for film-forming compositions capable of delivering actives to and through biological substrates. The cured films comprised therefrom, which reflect the benefits and characteristics known to be imparted by films that comprise both silicone and carbohydrate components.

SUMMARY OF THE INVENTION

According to one embodiment of the invention, a crosslinkable therapeutic composition is disclosed. The composition includes a saccharide-siloxane copolymer, a crosslinking agent, one or more active/inactive ingredients, and at least one of a solvent and solvent mixture. The saccharide-siloxane copolymer has the following formula: $R^2{}_aR^1{}_{(3-a)}SiO$—$[(SiR^2R^1O)_m$—$(SiR^1{}_2O)_n]_y$—$SiR^1{}_{(3-a)}R^2{}_a$. $R^1$ can be the same or different and comprises hydrogen, $C_1$-$C_{12}$ alkyl, an organic radical, or $R^3$-Q. Q comprises an epoxy, cycloepoxy, primary or secondary amino, ethylenediamine, carboxy, halogen, vinyl, allyl, anhydride, or mercapto functionality. m and n are integers between 0 and 10,000 and may be the same or different. Each a is independently 0, 1, 2, or 3. y is an integer such that the copolymer has a molecular weight less than 1 million. $R^1{}_{(3-a)}SiO$—$[(SiR^2R^1O)_m$—$(SiR^1{}_2O)_n]_y$—$SiR^1{}_{(3-a)}$ is an organosiloxane polymer component. $R_2$ has the formula $Z$-$(G^1)_b$-$(G^2)_c$, and there is at least one $R^2$ per copolymer. $G^1$ is a saccharide component comprising 5 to 12 carbons, b+c is 1-10, b or c can be 0, either b or c must be 1, $G^2$ is a saccharide component comprising 5 to 12 carbons additionally substituted with organic or organosilicon radicals, and Z is a linking group between the organosiloxane polymer component and the saccharide component and is independently selected from the group consisting of: —$R^3$—NHC(O)—$R^4$—, —$R^3$—NHC(O)O—$R^4$—, —$R^3$—NH—C(O)—NH—$R^4$—, —$R^3$——C(O)—O—$R^4$—, —$R^3$—S—$R^4$—,—$R^3$—CH(OH)—$CH_2$—O—$R^4$—,—$R^3$—CH(OH)—$CH_2$—NH—$R^4$—, and —$R^3$—N($R_1$)—$R^4$. $R^3$ and $R^4$ are divalent spacer groups comprising $(R^5)_r(R^6)_s(R^7)_t$, where at least one of r, s and t must be 1, $R^5$ and $R^7$ are either $C_1$-$C_{12}$ alkylene or $((C_1$-$C_{12})O)_p$ where p is any integer 1-50 and each $(C_1$-$C_{12})O$ may be the same or different, and $R^6$ is —N($R^8$)—, where $R^8$ is H or $C_1$-$C_{12}$ alkyl, or is Z—X, wherein Z is previously defined or $R^3$. The composition has therapeutic properties.

BRIEF DESCRIPTION OF THE DRAWINGS

FIG. 1. Illustrates drug release embodiments according to the present invention.

DETAILED DESCRIPTION

Accordingly, the present invention is based on the novel discovery of a film-forming composition and methods of making a film that avoids many of the prior art problems discussed above, and the films are therefore particularly useful in personal and healthcare applications. The presently inventive film-forming composition permits the combination into one technology of a substantive film former delivered in a pleasant carrier which is able to stabilize and release actives.

The present invention utilizes saccharide-derived polyhydroxyl siloxanes to form crosslinked networks via linking between the saccharides in the presence of a suitably reactive crosslinking agent, for example, borate or titanate esters and acids. The crosslinking occurring between the hydroxyl functionalities of the saccharide backbone of the copolymers is unique and forms a three-dimensional network having a unique matrix. Consequently, the films formed therefrom possess unique property profiles. While not being bound by theory, the resulting films combine the properties of siloxanes like, softness, vapor permeability, hydrophobicity, good aesthetic feel, adhesive release, & flexibility with the attributes of saccharides like substantivity to substrates containing hydroxyl groups or polar groups, e.g. wood, cellulose, cotton or skin. The unique hydrophilic & hydrophobic nature of these materials allows compatibility with a wide range of molecules, including biomaterial such as enzymes.

The resultant films have many uses in personal and healthcare applications, especially on the skin, where they can serve as, for example, topical drug delivery systems, masking systems for skin protection in dermal treatments, wound dressings and bandages for minor wounds, burns, acute and chronic wounds, skin sealants, skin protective films, scar treatments, exfoliation and hair remover products, deodorizing films, antiperspirant active and fragrance delivery systems, anti-wrinkle patches and moisturizing masks, wherein said film applications have benefits in topical therapies, wound care, surgical closure, scar care, underarm care, foot care, body and face skin care, cosmetics, make-up and foundations. They can likewise be used on other biological surfaces such as hair, nails, teeth, eyes, and mucous membranes as well as similar applications on animals other than humans and a variety of applications on flora.

The present invention relates to using certain formulations for forming films on substrates, preferably biological substrates, where they can serve, for example, as barrier films, cosmetic films, drug delivery mechanisms, wound management devices and the like.

One embodiment of the invention provides a film forming composition. The film-forming composition comprises a) a saccharide-siloxane copolymer; b) a crosslinking agent; c) one or more active/inactive ingredients; and d) optionally, a solvent, or solvent mixture. The saccharide-siloxane copolymer has the following formula: $R_2aR_1(3-a)SiO$—$[(SiR_2R_1O)m$-$(SiR_12O)n]y$—$SiR_1(3-a)R_2a$ that is formulaically designated and also designated according to specific embodiment needs. The saccharide-siloxane copolymer is a reaction product of a functionalized organosiloxane polymer and at least one hydroxy-functional saccharide such that the organosiloxane component is covalently linked via a linking group to the saccharide component.

The film-forming composition may be cured and then employed in the manufacture of articles, or may be applied directly to a substrate and cured in situ to form a cohesive and substantive film. The composition provides the capability of controlled release of the active or inactives in a variety of suitable cosmetics, pharmaceutical and medical applications.

When applied and cured in situ, the substrate can be any kind of biological tissue of vegetal, animal or human origin. For example, in specific human applications, the substrate may be skin, scar, corn, blister, wounded tissue, lip, nail, hair, eye-hair, mucosa, or the like.

Other embodiments provide articles of manufacture including films, bandages, topical and transdermal drug delivery patches, cosmetic delivery vehicles and wound dressings comprising the novel film-forming compositions.

These and other embodiments of the present invention will be more fully understood by reference to the detailed description and Examples set forth below.

The present invention provides novel film-forming compositions comprising crosslinkable saccharide-siloxane copolymers wherein the crosslinking substantially occurs between the hydroxy-functional groups of the saccharide components, and cured films comprising the crosslinked networks. The crosslinking occurring between the hydroxyl functionalities of the saccharide backbone of the copolymers is unique and forms a three-dimensional network having a unique matrix. Consequently, the films formed therefrom possess unique property profiles. The resulting films combine the properties of siloxanes, for example, softness, vapor permeability, hydrophobicity, good aesthetic feel, adhesive release, & flexibility with the attributes of saccharides like substantivity to substrates containing hydroxyl groups or polar groups, e.g. wood, cellulose, cotton or skin. The unique hydrophilic & hydrophobic nature of these materials allows compatibility with a wide range of molecules, including biomaterial such as enzymes. The cross-linked networks are particularly suitable for the entry and controlled release of actives and inactives and the film-forming compositions comprise active and/or inactive ingredients.

The film-forming compositions may be used as adhesive release films on biological surfaces, for topical administration of medicaments or other benefit-conferring actives, as protective barriers, or as wound dressings, or for purposes of transdermal release of the active or inactive ingredients. These films may also provide film-forming attributes for personal care products for hair, skin or antiperspirants. The crosslinkable composition in solvents may provide gellant properties desirable for other applications. Articles of manufacture comprising the novel film forming compositions may be adapted for a variety of useful functions, including but not limited to providing preservative, protective, defensive, and/or reactive functions to textiles and clothing, including those intended to be worn in the context of provision or receipt of health care services or during military engagement.

One embodiment is directed to a film-forming composition. The film-forming composition comprises: a) a saccharide-siloxane copolymer; b) a crosslinking agent; c) one or more active/inactive ingredients; and d) optionally, a solvent, or solvent mixture. The saccharide-siloxane copolymer has the following formula:

wherein $R_1$ can be the same or different and comprises hydrogen, C1-C12 alkyl, an organic radical, or $R_3$-Q, Q comprises an epoxy, cycloepoxy, primary or secondary amino, ethylenediamine, carboxy, halogen, vinyl, allyl, anhydride, or mercapto functionality, m and n are integers between 0 and 10,000 and may be the same or different, a is independently 0, 1, 2, or 3, y is an integer such that the copolymer has a molecular weight less than 1 million, $R_1(3-a)SiO—[(SiR_1O)m-(SiR_12O)n]y—SiR_1(3-a)$ comprises an organosiloxane polymer component, $R_2$ has the formula Z-(G1)b-(G2)c, and there is at least one $R_2$, wherein G1 is a saccharide component comprising 5 to 12 carbons, b+c is 1-10, b or c can be 0, either b or c must be 1, G2 is a saccharide component comprising 5 to 12 carbons additionally substituted with organic or organosilicon radicals, Z is a linking group between the organosiloxane polymer component and the saccharide component and is independently selected from the group consisting of:
—$R_3$—NHC(O)—$R_4$—;
—$R_3$—NHC(O)O—$R_4$—;
—$R_3$—NH—C(O)—NH—$R_4$—;
—$R_3$—C(O)—O—$R_4$—;
—$R_3$—O—$R_4$—;
—$R_3$—S—$R_4$—;
—$R_3$—CH(OH)—CH2-O—$R_4$—;
—$R_3$—CH(OH)—CH2-NH—$R_4$—; and
—$R_3$—N($R_1$)—$R_4$, and $R_3$ and $R_4$ are divalent spacer groups comprising $(R_5)r(R_6)s(R_7)t$, where at least one of r, s and t must be 1, and $R_5$ and $R_7$ are either C1-C12 alkyl or ((C1-C12)O)p where p is any integer 1-50 and each (C1-C12)O may be the same or different, $R_6$ is —N($R_8$)-, where $R_8$ is H or C1-C12 alkyl.

The saccharide-siloxane copolymer is a reaction product of a functionalized organosiloxane polymer and at least one hydroxy-functional saccharide such that the organosiloxane component is covalently linked via the linking group, Z, to the saccharide component.

According to specific embodiments, the saccharide-siloxane copolymer comprises a hydroxyl functionality of at least three and the at least one polyhydroxyl-functional saccharide comprises an aldonic acid or an oligoaldonic acid. In more specific embodiments the aldonic acid or the oligoaldonic acid comprises a lactone, and in very specific embodiments the lactone comprises a gluconolactone or lactobionolactone. Examples of suitable linking groups include, but are not limited to, an amide, an amino, a urethane, a urea, an ester, an ether, a thioether, or an acetal linking group. According to a preferred embodiment, the saccharide-siloxane is the reaction product of a gluconolactone with an aminopropyl-terminated polydimethylsiloxane whereby a polydimethylsiloxane having pendant aminoethylaminoisobutyl groups is reacted with gluconolactone at 1:1 primary amine:lactone stoichiometry.

The crosslinking agent comprises any agent capable of crosslinking a hydroxyl-functional polymer. The crosslinker may be selected from the following non-limiting list: boric acid, borate ester (e.g. tri-n-propyl borate, triisopropanolamine borate), alkyl boronic acid or ester (e.g. phenyl boronic acid), titanate, (e.g. titanium isopropoxide, diisopropoxytitanium bis(acetylacetonate)), zirconate, glyoxal, gluteraldehyde, epichlorohydrin, urea-formaldehyde, zirconium ammonium carbonate, salt of a multivalent ion, bifunctional epoxy or glycidyl compounds (e.g. 1,4 butanediol diglycidyl ether), di-(N-hydroxymethyl)urea, di-isocyanate (e.g. toluene diisocyante, hexamethylene diisocyanate), 2-chloro N,N di-ethylacetamide, sodium trimetaphosphate, phosphorous oxychloride, acrolein, N-methyl urea, dicarboxylic acid, bisacid chloride, dialkyldichlorosilane (e.g. dimethyldichlorosilane), alkyltrichlorosilane (e.g. Methyltrichlorosilane), reactive siloxane resin, and combinations thereof.

According to another embodiment, the film-forming composition further comprises one or more additional saccharide-siloxane copolymers and suitable cross linkers to form a blended film-forming composition. These blends may be designed to confer more than one benefit according to the copolymers selected.

Once delivered onto a biological substrate, the film-forming composition cures to form a cohesive and substantive film. The present inventive compositions are easy to cure, and cure readily with exposure to ambient conditions. Another embodiment of the present invention is directed to a method for delivering at least one active or inactive agent either topically to a biological substrate, or transdermally through a biological substrate. According to one specific embodiment, the film-forming composition is applied wet to the biological substrate and the composition cures in situ to form a film directed on the biological substrate. In another specific embodiment, the film-forming composition is first cured and then applied adhesively to the biological substrate.

The one or more active or/and inactive ingredients contemplated for inclusion in the film-forming compositions may be selected from the following: a catalyst; a filler; a pigment; a UV stabilizer; a fragrance; an essential oil; a thermal stabilizer; a rheology modifier; a thickener; an adhesion promoter; a biocide; a preservative; an enzyme; a peptide; a pressure sensitive adhesive; a surface-active agent; a pharmaceutical active; a cosmetic ingredient; a resin; and an aqueous ingredient. The substrate can be any kind of biological tissue from vegetal, animal or human origin. For example in human application, the substrate can be skin, scar, corn, blister, wounded tissue, lip, nail, hair, eye-hair, or mucosa.

According to specific embodiments, the biological substrate comprises skin, and, more specifically, human skin. The film may be useful for the treatment of cosmetic, medical or pharmaceutical indications, and may be incorporated into such articles of manufacture as wound dressings, bandages, topical or transdermal drug delivery patches, cosmetic compositions, or fragrance delivery patches. In particular embodiments, the wound dressing may comprise a film-forming composition wherein the active agent comprises one or more antibiotics, biocides or fungicides.

According to another embodiment, a transdermal drug delivery patch is provided comprising the novel film-forming compositions. The active is typically dispersed through out the cross-linked matrix and the active or inactive ingredients diffuse passively from the film or patch through the skin. The stratum corneum is the top most layer of skin that serves as the greatest barrier to drug diffusion. For certain desired agents, this natural barrier significantly reduces or prevents passive diffusion. In these instances enhancing devices, such as devices that create micropores in the stratum corneum, including, for example, microstructured arrays, sometimes called microneedles, that, when applied to the skin, painlessly create micropores in the stratum corneum without causing bleeding, may be suitably employed. These micropores offer lower resistance to drug diffusion than normal skin without micropores. Ablation of the stratum corneum from the epidermal layer is also a well-known enhancement process and includes, for example, ablation by laser systems. The inventive patch comprising the film-forming composition may then be applied to the ablated area to achieve transdermal delivery. Transdermal delivery via the novel films and patches is particularly useful for delivery of medicaments or pharmaceutical agents targeting systemically treatable conditions.

Excipients may be added to the film-forming composition to improve drug solubility and stability in the formulation and enhance the permeation of the drug across the skin. Chemical permeation enhancers are known in the art and are suitable excipients for inclusion in the present inventive formulations.

Methods for making the film-forming compositions are also provided. In one such embodiment the method comprises the steps of: a) dissolving a saccharide-siloxane copolymer in a suitable solvent to form a solution; b) dissolving at least one crosslinking agent in a suitable solvent to form a solution; c) adding the solution from b) into the solution from a) and mixing until b) is dispersed in a). The saccharide-siloxane copolymer comprises a reaction product of a functionalized organosiloxane polymer and at least one polyhydroxy-functional saccharide such that the organosiloxane polymer is covalently linked via a linking group to at least one polyhydroxyl-functional saccharide. Active or nonactive ingredients are preferably added to the composition prior to curing. Other additives are optional and may be included at none, one, some or all of steps a), b) and c), and are mixed until dispersed. Some agents or additives may require pre-dissolution in a suitable vehicle such as a solvent. The degree to which the additive incorporates into the matrix, and the ionic character of the additive influence the timeframe of addition. Additives may include but are not limited to: d) a catalyst; e) a filler; f) a pigment; g) a UV stabilizer; h) a thermal stabilizer; i) a rheology modifier; j) a thickener; k) an adhesion promoter; I) a biocide; m) a preservative; n) an enzyme; o) a peptide; p) a pressure sensitive adhesive, or any surface active agent. r) a cosmetic active, s) an antiperspirant compound, t) a UV screen agent, u) an active pharmaceutical ingredient (API), v) an insecticide, w) an anti-parasitic agent, or x) a fertilizer Alternatively, the saccharide siloxane can be prepared in the carrier solvent, eliminating the need to first isolate the saccharide siloxane. A cutback method is necessary to incorporate the silica because of the reduced sugar siloxane solution viscosity. This is done by alternating small increment additions of the silica filler and sugar siloxane solution to the formulation followed by mixing.

Film embodiments include for example, topical drug delivery systems, masking systems for skin protection in dermal treatments, wound dressings and bandages for minor wounds, burns, acute and chronic wounds, skin sealants, skin protective films, scar treatments, exfoliation and hair remover products, deodorizing films, antiperspirant active and fragrance delivery systems, anti-wrinkle patches and moisturizing masks, wherein said film applications have benefits in topical therapies, wound care, surgical closure, scar care, underarm care, foot care, body and face skin care, cosmetics, make-up and foundations. They can likewise be used on other biological surfaces such as hair, nails, teeth, eyes, and mucous membranes as well as similar applications on animals other than humans and a variety of applications on flora.

The present formulations can also comprise fillers. The fillers can include, but are not limited to, ground, precipitated, and colloidal calcium carbonates which can be untreated or treated with stearate or stearic acid; reinforcing silicas such as fumed silicas, precipitated silicas, and hydrophobed silicas; crushed quartz, ground quartz, alumina, aluminum hydroxide, titanium dioxide, diatomaceous earth, iron oxide, carbon black, and graphite. One class of preferred fillers are synthetic silicas where the surfaces of the silica are modified with silicon compounds to produce a hydrophobic behavior. These materials differ from one another in surface area, the silicon compound used to treat the silica, and the extent of surface treatment. Such materials are surprisingly able to reduce the viscosity of the film forming formulation. In addition, resinous reinforcing fillers can be used herein to form transparent films. Silica, calcium carbonate and resinous fillers are especially preferred. Specific examples include Cab-O-Sil® PTG, Cab-O-Sil® TS-530 treated filler, Aerosil® R8200 treated filler, and Wacker HDX H2000 treated filler.

If used, the amount of filler in the formulation is generally that amount which provides the desired properties to the uncured formulation such as viscosity, thixotropy, pigmentation, and UV protection. The amount of filler also depends upon the cured physical properties desired such as tensile strength, elongation, and durometer. Finally, the amount of filler also depends on the amounts of other components added, as well as the hydroxyl content of the specific filler used. Typically, this is an amount in the range of about 0.1 to 25 weight percent based on the total weight of the formulation. Preferably, the filler is added in amounts from about 2 to 15 weight percent on the same basis. The filler may be a single filler or a mixture of two or more fillers.

The formulation can also comprise fluorinated fluids, resins, organosiloxane polymers and resins. These materials provide additional properties to the film including but not limited to: softness, flexibility, higher adhesion to substrates like skin and plastic films, pressure sensitive adhesive surface activity, lower coefficient of friction, lubricity, or modified permeability. Examples of fluorinated fluids are fluorinated siloxanes, trifluoropropylmethyl siloxane. Examples of resins are rosin type resins and acrylic polymer resins. Examples of organosiloxane polymers are silicone polyethers, silicone polyamides, and silicone acrylic copolymers. Examples of organosiloxane resins are siloxane MQ resins.

Therapeutic active agents which may be employed according to the present invention include, for example, anti-acne agents, antibiotic, antiseptic, antifungal, antibacterial, antimicrobial, biocides, anti-inflammatory, astringents, hormones, anticancer agents, smoking cessation compositions, cardiovascular, histamine blocker, bronchodilator, analgesic, anti-arrhythmic, antihistamine, alpha-I blocker, beta blocker, ACE inhibitor, diuretic, antiaggregant, sedative, tranquilizer, anticonvulsant, anticoagulant agents, vitamins, antiaging agents, agents for treating gastric and duodenal ulcers, anticellulites, proteolytic enzymes, healing factors, cell growth nutrients, peptides and others. Specific examples of suitable therapeutic active agents include silver derivatives, penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, benzocaine, sulphonamides, ticonazole, perbuterol, furosamide, prazosin, prostaglandins, salbutamol, indomethicane, diclofenac, glafenine, dipyridamole, theophylline and retinol.

In addition to the therapeutic or diagnostic materials, active ingredients may be cosmetics such as perfumes, UV protectors, shaving products, deodorants or the like. Suitable cosmetics are known to those skilled in the art.

The proportion of the active agent employed in the present invention is chosen in accordance with the concentration of the active agent required in the composition to deliver the dosage required at the proposed delivery rate. This may vary within a wide range such as from 0.1 to about 70 weight percent, preferably 0.1 to 20 weight percent, of the final composition.

The film-forming compositions may also contain other additional ingredients. One advantageous additive is a water scavenger to prevent early curing of the formulation. Other optional ingredients include colorants, colored indicators, other diluents, extenders such as silicone fluids, silicone resins, excipients employed in pharmacy, compounds intended to perform as pH buffers in controlling the environment immediately in and around the formulation, stabilizers, preservatives, surfactants for cellular formulations such as fluorinated silicones, processing aids such as cyclic or linear polydiorganosiloxanes, bioadhesive materials, and hydrophilic, modulating and swellable components or polymers as set forth in EP Publication 465,744. Still other additional ingredients include absorbents for wounds, alginate, polysaccharides, gelatin, collagen, and materials that can decrease the friction on the surface of the cured film and/or change its gloss.

Some additional examples of the cosmetics, personal care, and cosmeceutical ingredients and pharmaceutical excipients that may be used herein may be found in the CTFA ingredient Database and the handbook of pharmaceutical excipients and can include, for example, essential oils, absorbents, anticacking agents, antioxidants, antistatic agents, astringents, binders, buffering agents, bulking agents, chelating agents, colorants, cosmetic astringents, cosmetic biocides, deodorant agents, emollients, external analgesics, film formers, flavoring agents, fragrance ingredients, humectants, lytic agents, moisturizing agents, occlusivity enhancers, opacifying agents, oxidizing and reducing agents, penetration enhancers, pesticides, plasticizers, preservatives, skin bleaching agents, skin conditioning agents, skin protectants, slip modifiers, solubilizing agents, solvents, sunscreen agents, surface modifiers, surfactants and emulsifying agents, suspending agents, thickening agents, viscosity controlling agents including increasing or decreasing agents, UV light absorbers, Cosmetic, personal care and cosmeceutical ingredients, and pharmaceutical excipients which may be employed are selected, for example, from the following chemical classes: alcohols, fatty alcohols and polyols, aldehydes, alkanolamines, alkoxylated alcohols (e.g. polyethylene glygol derivatives of alcohols and fatty alcohols), alkoxylated amides, alkoxylated amines, alkoxylated carboxylic acids, amides including salts (e.g. ceramides), amines, amino acids including salts and alkyl substituted derivatives, esters, alkyl substituted and acyl derivatives, polyacrylic acids, acrylamide copolymers, adipic acid copolymers, alcohols, aminosilicones, biological polymers and derivatives, butylene copolymers, carbohydrates (e.g. polysaccharides, chitosan and derivatives), carboxylic acids, carbomers, esters, ethers and polymeric ethers (e.g. PEG derivatives, PPG derivatives), glyceryl esters and derivatives, halogen compounds, heterocyclic compounds including salts, hydrophilic colloids and derivatives including salts and gums (e.g. cellulose derivatives, gelatin, xanthan gum, natural gums), imidazolines, inorganic materials (clay, TiO2, ZnO), ketones (e.g. camphor), isethionates, lanolin and derivatives, organic salts, phenols including salts (e.g. parabens), phosphorus compounds (e.g. phosphate derivatives), polyacrylates and acrylate copolymers, protein and enzymes derivatives (e.g. collagen), synthetic polymers including salts, siloxanes and silanes, sorbitan derivatives, sterols, sulfonic acids and derivatives and waxes.

Examples of essential oils are Arnica (*Arnica Montana*), Basil (*Ocimum Basilicum*), Bergamot (*Citrus Bergamia*), Cedarwood (*Cedrus Atlantica*), Chamomile Roman (*Chamaemelum Nobile*), Cinnamon (*Cinnamomum Cassia*), Cinnamon Bark (*Cinnamomum Verum*), Cistus Labdanum (*Cistus Ladanifer*), Clary Sage (*Salvia Sclarea*), Clove (*Syzygium Aromaticum*) Eugenol, Coriander (*Coriandrum Sativum*), Cypress (*Cupressus Sempervirens*), Dill (*Anethum Graveolens*), Elemi (*Canarium Luzonicum*), Eucalyptus Dives (*Eucalyptus Dives*), Eucalyptus Globulus (Eucalyptus Globulus), Eucalyptus Polybractea (*Eucalyptus Polybractea*), Eucalyptus Radiata (*Eucalyptus Radiata*), Fennel (*Foeniculum Vulgare*), Fir Douglas (*Pseudotsuga Menziesii*), Fir White (*Abies Grandis*), Frankincense (*Boswellia Carteri*), Galbanum (*Ferula Gummosa*), Geranium (*Pelargonium Graveolens*), Ginger (*Zingiber Officinale*), Goldenrod (*Solidago Canadensis*), Gotu Kola (*Centella Asiatica*), Grapefruit (*Citrus Paradisi*), *Helichrysum* (*Helichrysum Italicum*), Hyssop (*Hyssopus Officinalis*), Idaho Balsam Fir (*Abies Balsamea*), Idaho Balsam Fir (*Abies Balsamea*), Jasmine (*Jasminum Officinale*), Juniper (*Juniperus Osteosperma, Juniperus Scopulorum*), Laurus Nobilis (*Laurus Nobilis*), Lavender (*Lavandula Angustifolia*), Ledum (*Ledum Groenlandicum*), Lemon (*Citrus Limon*), Lemongrass (*Cymbopogon Flexuosus*), Marjoram (*Origanum Majorana*), Melaleuca Alternifolia Or Tea Tree Oil (*Melaleuca Alternifolia*), Melaleuca Ericifolia (*Melaleuca Ericifolia*), Melissa (*Melissa Officinalis*), Mountain Or Winter Savory (*Satureja Montana*), Myrrh (*Commiphora Myrrha*), Myrtle (*Myrtus Communis*), Nutmeg (*Myristica Fragrans*), Orange (*Citrus Aurantium*), Oregano (*Origanum Compactum*), Palmarosa (*Cynopogon Martinii*), Patchouly (*Pogostemon Cablin*), Pepper, Black (*Piper Nigrum*), Peppermint (*Mentha Piperita*), Petit Grain (*Citrus Aurantium*), Pine (*Pinus Sylvestris*), Ravensara (*Ravensara Aromatica*), Rose (*Rosa Damascena*), Rosemary (*Rosmarinus Officinalis*), Rosewood (*Aniba Rosaeodora*), Sage (*Salvia Officinalis*), Sandalwood (*Santalum Album*), Spearmint (*Mentha Spicata*), Spikenard (*Nardostachys Jatamansi*), Spruce (*Picea Mariana*), St John's Wort (*Hypericum Perforatum*), Tangerine (*Citrus Reticulata*), Tansy Idaho (*Tanacetum Vulgare*), Tarragon (*Artemisia Dracunculus*), Thyme (*Thymus Vulgaris*), Tsuga (*Tsuga Canadensis*), Valerian (*Valariana Officinalis*), Vetiver (*Vetiveria Zizanioides*), Western Red Cedar (*Thuja Plicata*), Wintergreen (*Gaultheria Procumbens*), Ylang Ylang (*Cananga Odorata*).

Non-limiting examples of antiacne agents include salicylic acid, benzoyl peroxide, vitamins, and sulfur, and non-limiting examples of antifungal agents are calcium undecylenate, undecylenic acid, zinc undecylenate, and povidone-iodine.

Examples of antimicrobial agents and biocides include, but are not limited to, alcohols, benzalkonium chloride, benzethonium chloride, hydrogen peroxide, methylbenzethonium chloride, phenol, poloxamer 188, povidone-iodine, polyhexamethylene biguanide hydrochloride, silver derivatives including salt and nano silver, and xylitol.

Examples of antioxidants include, but are not limited to, acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *camellia sinensis* oil, chitosan ascorbate, chitosan glycolate, chitosan salicylate, chlorogenic acids, cysteine, cysteine HCl, decyl mercaptomethylimidazole, erythorbic acid, d-limonene, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, Isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (melaleuca altemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, and zinc dibutyldithiocarbamate.

Examples of cosmetic biocides include, but are not limited to, aluminum phenolsulfonate, ammonium phenolsulfonate, bakuchiol, benzalkonium bromide, benzalkonium cetyl phosphate, benzalkonium chloride, benzalkonium saccharinate, benzethonium chloride, potassium phenoxide, benzoxiquine, benzoxonium chloride, bispyrithione, boric acid, bromochlorophene, camphor benzalkonium methosulfate, captan, cetalkonium chloride, cetearalkonium bromide, cetethyldimonium bromide, cetrimonium bromide, cetrimonium chloride, cetrimonium methosulfate, cetrimonium saccharinate, cetrimonium tosylate, cetylpyridinium chloride, chloramine T, chlorhexidine, chlorhexidine diacetate, chlorhexidine digluconate, chlorhexidine dihydrochloride, p-chloro-m-cresol, chlorophene, p-chlorophenol, chlorothymol, chloroxylenol, chlorphenesin, ciclopirox olamine, climbazole, cloflucarban, clotrimazole, coal tar, colloidal sulfur, o-cymen-5-ol, dequalinium acetate, dequalinium chloride, dibromopropamidine diisethionate, dichlorobenzyl alcohol, dichlorophene, dichlorophenyl imidazoldioxolan, dichloro-m-xylenol, diiodomethyltolylsulfone, dimethylol ethylene thiourea, diphenylmethyl piperazinylbenzimidazole, domiphen bromide, 7-ethylbicyclooxazolidine, fluorosalan, formaldehyde, glutaral, hexachlorophene, hexamidine, hexamidine diisethionate, hexamidine diparaben, hexamidine paraben, hexetidine, hydrogen peroxide, hydroxymethyl dioxoazabicyclooctane, ichthammol, isopropyl cresol, lapyrium chloride, lauralkonium bromide, lauralkonium chloride, laurtrimonium bromide, laurtrimonium chloride, laurtrimonium trichlorophenoxide, lauryl isoquinolinium bromide, lauryl isoquinolinium saccharinate, laurylpyridinium chloride, mercuric oxide, methenamine, methenammonium chloride, methylbenzethonium chloride, myristalkonium chloride, myristalkonium saccharinate, myrtrimonium bromide, nonoxynol-9 iodine, nonoxynol-12 iodine, olealkonium chloride, oxyquinoline, oxyquinoline benzoate, oxyquinoline sulfate, PEG-2 coco-benzonium chloride, PEG-10 coco-benzonium chloride, PEG-6 undecylenate, PEG-8 undecylenate, phenol, o-phenylphenol, phenyl salicylate, piroctone olamine, sulfosuccinylundecylenate, potassium o-phenylphenate, potassium salicylate, potassium troclosene, propionic acid, PVP-iodine, quaternium-8, quaternium-14, quaternium-24, sodium phenolsulfonate, sodium phenoxide, sodium o-phenylphenate, sodium shale oil sulfonate, sodium usnate, thiabendazole, 2,2'-thiobis(4-chlorophenol), thiram, triacetin, triclocarban, triclosan, trioctyldodecyl borate, undecylenamidopropylamine oxide, undecyleneth-6, undecylenic acid, zinc acetate, zinc aspartate, zinc borate, zinc chloride, zinc citrate, zinc cysteinate, zinc dibutyldithiocarbamate, zinc gluconate, zinc glutamate, zinc lactate, zinc phenolsulfonate, zinc pyrithione, zinc sulfate, and zinc undecylenate.

External analgesics are also suitable ingredients and include, for example, benzyl alcohol, *capsicum* oleoresin (*capsicum frutescens* oleoresin), methyl salicylate, camphor, phenol, capsaicin, juniper tar (*juniperus oxycedrus* tar), phenolate sodium (sodium phenoxide), *capsicum* (*capsicum frutescens*), menthol, resorcinol, methyl nicotinate, and turpentine oil (turpentine). Oxidizing agents suitably employable include, for example, ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, and zinc peroxide, while reducing agents suitably employable include, for example, ammonium bisufite, ammonium sulfite, ammonium thioglycolate, ammonium thiolactate, cystemaine hcl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, and zinc formaldehyde sulfoxylate.

A non-limiting example of a suitable skin bleaching active agent is hydroquinone, and examples of skin protectants include, but are not limited to, allantoin, aluminum acetate, aluminum hydroxide, aluminum sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, and zinc oxide.

Nonlimiting examples of sunscreen agents include aminobenzoic acid, cinoxate, diethanolamine methoxycinnamate, digalloyl trioleate, dioxybenzone, ethyl 4-[bis(hydroxypropyl)]aminobenzoate, glyceryl aminobenzoate, homosalate, lawsone with dihydroxyacetone, menthyl anthranilate, octocrylene, octyl methoxycinnamate, octyl salicylate, oxybenzone, padimate O, phenylbenzimidazole sulfonic acid, red petrolatum, sulisobenzone, titanium dioxide, and trolamine salicylate, and examples specifically of UV light absorbing agents include acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic acid, benzyl salicylate, bornelone, bumetriozole, butyl methoxydibenzoylmethane, butyl PABA, ceria/silica, ceria/silica talc, cinoxate, dea-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium d istyrylbiphenyl triaminotriazine stilbened isulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, octyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, tea-phenylbenzimidazole sulfonate, tea-salicylate, terepbthalylidene dicamphor sulfonic acid, titanium dioxide, triPABA panthenol, urocanic acid, and va/crotonates/methacryloxybenzophenone-1 copolymer.

Since the formulation cures at room temperature after evaporation of the solvent, the component materials can be mixed and stored in a evaporation proof container. It can be stored in a plurality of containers prior to use to inhibit curing or inhibition when co-formulated with excipients and actives prior to use. Suitable containers include, for example, single use containers (e.g., foil packets, tubes, soft capsules, blisters, wipes) or multiple use containers (e.g. roll-on, tube with foam pad, pen like system, pumps and sprays, brush-in-bottle). It is often desirable to put a diluent in both containers.

According to particular methods of the invention, the curable formulation is applied to the desired site or, alternatively, the component materials of the invention can be applied onto the desired site in a manner that causes mixing. The formulation reacts when the solvent evaporates and results in a cured composition. Preferably, the formulations are applied on a biological surface including, but not limited to animal bodies (e.g., human or other animal) and flora.

The formulations of the invention can be applied, for example, by rubbing, painting, spraying, wiping, or any other conventional method of applying thin films.

As noted above, when the formulation is applied, it dries and cures rapidly at room temperature in the presence of moisture (e.g., within 10 minutes, usually within 1-2 minutes). For example, the formulation will cure rapidly on a human or other animal body. If used on an animal, this can minimize the amount time necessary to keep the area immobile while curing takes place.

The final composition can be in the form of a gel or an elastomer and it can have pores (e.g., foams) or it can be pore-free. If the final composition has pores, the formulations might contain materials such as blowing agents to form the pores.

The present invention offers numerous advantages over the prior art. The method described herein allows for a simple method of forming a film on a substrate. As such, a skilled practitioner is not required for application. Moreover, the composition can be formed into a wide variety of shapes and have selected combinations of properties (e.g. bioadhesion, release rate and release profile). Similarly, the formulations and processes described herein don't involve severe conditions (e.g. high temperatures or pressures) that might damage any active agents or substrates used.

The formulations and resultant compositions herein are generally acceptable on many biological surfaces. The composition may be formed on intact or damaged skin or in a natural or artificial cavity of the body. The cavity may be, for example, the ocular, buccal, nasal, aural, vaginal or rectal cavity or a cavity formed, for example, in a tooth or an open wound.

The resultant films are typically thin and non-tacky. Films on the order of up to 500 microns (e.g., 2.5 microns to 250 microns) are often obtained. These films can have many physical properties from gels to elastomers so that they are able to withstand many of the pressures exerted during normal activities of a patient.

The invention allows for a film former that can be applied to skin, intact or damaged, in order to form a protective barrier or deliver an active (cosmetic or pharmaceutical). The success criteria are film forming property, non stinging if applied to damaged skin, substantivity (e.g. long lasting wear time), resistance to water, removability, adjustable permeability, permeability to actives, ability to be co-formulated, and stability.

The following examples are set forth to illustrate certain embodiments of the invention, and should not be construed as limiting the scope of the invention as defined by the claims. Unless indicated, all parts are by weight and all viscosities are at 25° C.

Example 1

This Example illustrates formulation of saccharide-siloxane composition XX-5501. Certain formulation embodiments of the present invention are made by blending, for example, the components listed in the silicone and organic excipient lists below, with the saccharide-siloxane composition designated herein as XX-5501 and prepared as per the protocol set forth below.

The polymer GL-8211 used to prepare the saccharide-siloxane composition XX-5501 is the reaction product of a gluconolactone with an aminopropyl-terminated polydimethylsiloxane according to the following procedure: DC® 2-8211 Polymer (Dow Corning Corp., Midland, Mich.), a 1000 cst. polydimethylsiloxane with pendant aminoethylaminoisobutyl groups (approximately 1.9 mole percent), is reacted with gluconolactone at 1:1 primary amine:lactone stoichiometry in methanol at 50° C. Upon completion of the reaction, the methanol is removed with rotary evaporation. The resulting material has a gum-like consistency.

The saccharide siloxane composition XX-5501 is prepared according to the following procedure: 45 g of GL-8211 saccharide-siloxane as prepared above, is diluted with a 90/10 by weight solution of 0.65 cSt 200 Fluid (Dow Corning Corp, Midland Mich.) and 200 proof ethanol until a 50% copolymer concentration is achieved. The dilution is accomplished by sequential additions of the solvent followed by mixing on a Hauschild Speedmixer™ centrifugal mixer (Flacktek, Inc. Landrum, S.C.) until homogenous. The crosslinker is a 10% by weight solution of phenyl boronic acid (Sigma-Aldrich Co., St. Louis, Mo.) in 200 proof ethanol. Cab-o-sil TS-530 is a hexamethyldisilazane treated silica (Cabot Co. Boston, Mass.). The saccharide-siloxane solution, treated silica, and crosslinker solutions are mixed on a Hauschild Speedmixer™ centrifugal mixer (Flacktek, Inc. Landrum, S.C.) until homogenous.

Batches of XX-5501 were prepared with different levels of cross-linker:
- 19786-93 contained 0.7 percent of cross-linker phenyl boronic acid. 41.6 wt. % solid content.
- 19809-129A contained 0.5 percent of cross-linker phenyl boronic acid. 44 wt. % solid content.
- 19809-129B contained 2.0 percents of cross-linker phenyl boronic acid. 42 wt. % solid content.

Exemplary Active and Inactive Ingredients
a. Silicone Excipients (Available from Dow Corning Corporation)
- Dow Corning® 193 fluid—INCI name: PEG-12 dimethicone
- Dow Corning® 2503 cosmetic wax—INCI name: Stearyl dimethicone-CAS # 67762-83-8
- Dow Corning FA 4001 CM Silicone Acrylate—INCI name: cyclopentasiloxane and Acrylates/Polymethylsiloxymethacrylate copolymer
- Dow Corning FA 4002 ID Silicone Acrylate—INCI name: Isododecane and Acrylates/Polymethylsiloxymethacrylate copolymer b. Organic Excipients
- Arnica Montana tincture—Composition: Alcohol and water and Arnica montana flower extracted, Supplier: Dolisos
- *Centella Asiatica* dry extract—INCI name: *Centella asiatica* dry extract, CAS # 84696-21-8, Supplier: Linnea
- *Hypericum Perforatum* dry extract—FNC™ name: *Hypericum perforatum* flower/leaf/stem extract, CAS # 84082-80-4, Supplier: Linnea
- Calcium Alginate—INCI name: *Calcium alginate*, CAS # 9002-35-0, Supplier: Sigma-Aldrich
- Reach 103—INCI name: *Aluminum chlorohydrate*, CAS # 1327-41-9, Supplier: Reheis
- Essential oil of *Aniba Rosaedora*—INCI name: *Aniba rosaedora* (rosewood) wood oil, CAS # 8015-77-8, Supplier: Plaisir d'essence
- Essential oil of *Cinnamomum Cassia*—INCI name: *Cinnamomum Cassia* leaf oil, CAS # 8007-77-8, Supplier: Plaisir d'essence
- Essential oil of *Eucalyptus Radiata*—INCI name: *Eucalyptus radiate*, CAS # n.a., Supplier: Plaisir d'essence
- Essential oil of *Eucalyptus Citriodora*—INCI name: *Eucalyptus Citriodora* oil, CAS # 8000-48-4, Supplier: Plaisir d'essence
- Essential oil of *Eucalyptus Globulus*—CAS # 8000-48-4, Supplier: Plaisir d'essence
- Essential oil of Eucalyptus *Dives* ssp *Piperitoniferum*—CAS # n.a., Supplier: Plaisir d'essence
- Essential oil of *Eucalyptus Smithii*—CAS # n.a., Supplier: Plaisir d'essence
- Essential oil of *Mentha Piperita*—CAS # 8006-90-4, Supplier: Plaisir d'essence
- Essential oil of *Cinopogon Martini*—CAS #8014-19-5, Supplier: Plaisir d'essence
- Lidocaine—Formule: C14H22N2O, CAS #137-58-6, Supplier: Sigma-Aldrich
- Ethyl 4-Aminobenzoate PH Eur—Technical name: benzocaine, CAS #94-09-7, Supplier: Sigma-Aldrich
- NaCl/Sodium Chloride—INCI name: sodium chloride, CAS #7647-14-5, Supplier: Sigma-aldrich
- Castor oil—INCI name: *Ricinus communis* (CAStor) seed oil, CAS # 8001-79-4, Supplier: Sigma-Aldrich
- Absolute ethanol—INCI name: Alcohol, CAS # 64-17-5, Supplier: Fisher-bioblock
- Propylene glycol—INCI name: Propylene glycol, CAS # 57-55-6, Supplier: Sigma-Aldrich
- Glycerin—INCI name: Glycerin, CAS # 56-81-5, Supplier: Sigma-Aldrich Example 2

This Example illustrates a formulation of the film-forming cross-linkable saccharide-siloxane and one or more active/inactive ingredients according to certain embodiments of the present invention.

Preparation Procedure:
a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.

b. film of wet saccharide siloxane containing the active or inactive ingredient is coated on fluorinated liner using lab coating table and 100 μm shims.

Testing Procedure:

a. The drying time is measured with a chronometer. The film is considered dry when it doesn't stick to the finger.

b. Film appearance—The film is observed visually for shine, transparency through the film, transparency on a paper (could we read a text through the film when the film is on a book), general appearance smooth or rough.

c. Mechanical properties—A rectangle of 2 cm×5 cm is cut in each film and evaluated for cohesion by stretching the film between fingers.

TABLE 1

| Ingredient | XX-5501 #19786-93 (wt. %) | Ingredient (wt. %) | Drying Time (seconds) | Cohesion | Stickiness | Appearance |
|---|---|---|---|---|---|---|
| XX-5501 | 100 | 0 | 25-30 | Good | Dry | Transparent |
| Propylene glycol | 98.6 | 2.4 | 30 | Low | Sticky | |
| Propylene glycol | 88 | 12 | 35 | Low | Sticky | |
| Propylene glycol | 76 | 24 | Wet | Low | Wet | PG droplets |
| Arnica Montana tincture | 98.6 | 2.4 | 24 | Good | Dry | White |
| Arnica Montana tincture | 88 | 12 | 35 | Good | Dry | White, opaque |
| Arnica Montana tincture | 76 | 24 | 47 | Good | Dry | White, opaque |
| NaCl | 98.6 | 2.4 | 30 | Good | Dry | Visible salt grain |
| NaCl | 88 | 12 | 30 | Good | Dry | Visible salt grain |
| NaCl | 76 | 24 | 28 | Good | Dry | |
| Aluminum chlorohydrate | 98.6 | 2.4 | 33 | Good | Dry | White |
| Aluminum chlorohydrate | 88 | 12 | 28 | Good | Dry | Small grain |
| Aluminum chlorohydrate | 76 | 24 | 29 | Good | Dry | Small grain |
| Cinnamomum Cassia | 88 | 12 | 22 | Good | Dry | Yellow |
| Cinnamomum Cassia | 76 | 24 | 27 | Good | Dry | Yellow |
| Ethanol | 76 | 24 | | Good | Dry | Like XX001 |
| Lidocaine | 88 | 12 | 32 | Fair | Dry | Opaque |
| Lidocaine | 76 | 12 | | Fair | Dry | Opaque |
| Cinopogon Martini | 76 | 24 | | Good | Slow drying | |
| Aniba Rosaedora | 76 | 24 | | Good | Slow drying | |
| Eucalyptus Radiata | 76 | 24 | | Good | Dry | Yellow |
| Mentha Piperita | 76 | 24 | | Good | Slow drying | |

Example 3

This Example illustrates the formulation of XX-5501 batch 19809-129, A and B with one or more actives/inactives according to certain embodiments of the present invention.

Preparation Procedure:

a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.

b. A film of wet saccharide-siloxane containing the ingredient is coated on fluorinated liner using lab coating table and 100 μm shims.

Testing Procedure:

a. The dying time is measured with a chronometer. The film is considered dry when it doesn't stick to the finger.

TABLE 2

| Ingredient | Ingredient (wt. %) | XX-5501 #19809-129A Drying Time (seconds) | XX-5501 #19809-129B Drying Time (seconds) |
|---|---|---|---|
| NO | 0 | 20-30 | 20-30 |
| Arnica montana tincture | 1 | 25 | 31 |
| Centella Asiatica (dispersed in PG) | 1% of Centella | 45 | >30 |
| Propylene glycol | 10 | 90 | 34 |
| Propylene glycol | 1 | 35 | 33 |
| Hypericum Perforatum (dispersed in PG) | 1% of Hypericum | 40 | 138 |
| Calcium alginate | 1 | 28 | 27 |
| Aluminum chlorohydrate | 1 | 31 | 30 |
| Aniba Rosaedora | 1 | 27 | 29 |
| Cinnamomum Cassia | 1 | 32 | 37 |
| Eucalyptus Radiata | 1 | 22 | 21 |
| Mentha piperita | 1 | 32 | 33 |
| Cynopogon Martini | 1 | 29 | 48 |
| Lidocaine (dispersed in ethanol) | 1% of lidocaine | 34 | 38 |
| Benzocaine (dispersed in ethanol) | 1% of benzocaine | 44 | 37 |
| Ethanol | 2 | 52 | 43 |
| Ethanol | 4 | 48 | 51 |
| NaCl | 1 | 25 | 31 |
| Castor oil | 1 | 130 | 42 |
| Castor oil | 2 | 130 | 47 |

Example 4

Preparation Procedure:

a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.

b. A film of wet saccharide-siloxane containing the ingredient is coated on fluorinated liner using lab coating table and 100 μm shims.

Testing Procedure:

a. Film appearance, the film is observed visually for shine, transparency through the film, transparency on a paper (readability through the film), global appearance (smooth or rough).

TABLE 3

| Ingredient | Ingredient wt. % in XX-5501 #19809-129A | Shine | Smoothness | Transparency through the film | Ability to read a text though the film | Comment |
|---|---|---|---|---|---|---|
| XX-5501 #19809-129A | 0 | High | High | Medium | High | |
| *Arnica montana* tincture | 1 | High | High | Medium | High | |
| *Centella Asiatica* (dispersed in PG) | 1% of *Centella* | High | High | Medium | High | |
| Propylene glycol | 10 | High | High | Medium | High | |
| Propylene glycol | 1 | High | High | Medium | Medium | |
| *Hypericum Perforatum* (dispersed in PG) | 1% of *Hypericum* | High | High | High | High | yellow |
| Calcium alginate | 1 | High | Low | Medium | Medium | Grain |
| Aluminum chlorohydrate | 1 | Low | Low | Low | Low | |
| *Aniba Rosaedora* | 1 | High | High | Medium | Medium | Fragrance release |
| *Cinnamomum Cassia* | 1 | Low | High | Medium | Low | Yellow Fragrance release |
| *Eucalyptus Radiata* | 1 | Low | Low | Low | Low | Yellow Fragrance release |
| *Mentha piperita* | 1 | Low | Medium | Medium | High | Fragrance release |
| Cynopogon Martini | 1 | Medium | High | Medium | High | Fragrance release |
| Lidocaine (dispersed in ethanol) | 1% of lidocaine | Medium | High | Medium | High | |
| Benzocaine (dispersed in ethanol) | 1% of benzocaine | High | High | Medium | Medium | |
| Ethanol | 2 | Medium | High | Medium | Medium | |
| Ethanol | 4 | High | High | Medium | Medium | |
| NaCl | 1 | Medium | Low | Medium | Medium | Grain |
| Castor oil | 1 | Low | Medium | Medium | Medium | |
| Castor oil | 2 | Low | Medium | Medium | medium | |

Example 5

Preparation Procedure:

a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.

b. A film of wet saccharide-siloxane containing the ingredient is coated on fluorinated liner using lab coating table and 100 μm shims.

Testing Procedure:

a. mechanical properties—A rectangle of 2 cm×5 cm is cut in each film and evaluated for cohesion by stretching the film between fingers.

TABLE 4

| Ingredient | Ingredient wt. % in XX-5501 #19809-129A | Removability from fluorinated film | Elastic Modulus | Resistance to break | Elongation |
|---|---|---|---|---|---|
| XX-5501 #19809-129A | 0 | High | High | Medium | Low |
| *Arnica montana* tincture | 1 | High | High | Medium | Low |

TABLE 4-continued

| Ingredient | Ingredient wt. % in XX-5501 #19809-129A | Removability from fluorinated film | Elastic Modulus | Resistance to break | Elongation |
|---|---|---|---|---|---|
| *Centella Asiatica* (dispersed in PG) | 1% of *Centella* | High | Medium | Medium | High |
| Propylene glycol | 10 | High | Medium | Low | High |
| Propylene glycol | 1 | High | Low | Low | Low |
| *Hypericum Perforatum* (dispersed in PG) | 1% of *Hypericum* | Medium | Medium | Low | High |
| Calcium alginate | 1 | High | Medium | Medium | Low |
| Aluminum chlorohydrate | 1 | Medium | Medium | Medium | Low |
| *Aniba Rosaedora* | 1 | High | High | High | Low |
| *Cinnamomum Cassia* | 1 | High | High | High | Low |
| *Eucalyptus Radiata* | 1 | High | High | High | Low |
| *Mentha piperita* | 1 | High | Medium | Medium | Low |
| *Cynopogon Martini* | 1 | High | High | Medium | Low |
| Lidocaine (dispersed in ethanol) | 1% of lidocaine | High | Medium | High | Low |
| Benzocaine (dispersed in ethanol) | 1% of benzocaine | Medium | Medium | Medium | Medium |
| Ethanol | 2 | High | Medium | Medium | Low |
| Ethanol | 4 | Medium | Low | Medium | Low |
| NaCl | 1 | High | Medium | Medium | Low |
| Castor oil | 1 | High | Medium | Medium | Medium |
| Castor oil | 2 | Medium | Medium | Low | High |

Example 6

Preparation Procedure:

a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.

b. A film of wet saccharide-siloxane containing the ingredient is coated on fluorinated liner using lab coating table and 100 μm shims.

Testing Procedure:

a. Film appearance, the film is observed visually for shine, transparency through the film, transparency on a paper (readability of a through the film), global appearance smooth or rough.

TABLE 5

| Ingredient | Ingredient wt. % in XX-5501 #19809-129B | Shine | Smoothness | Transparency through the film | Ability to read a text though the film | Comment |
|---|---|---|---|---|---|---|
| XX-5501 #19809-129B | 0 | Medium | High | Medium | High | |
| *Arnica Montana* tincture | 1 | High | High | High | High | |
| *Centella Asiatica* (dispersed in PG) | 1% of *Centella* | High | High | High | High | |
| Propylene glycol | 10 | Medium | Medium | High | High | Tacky |
| Propylene glycol | 1 | High | High | High | High | |
| *Hypericum Perforatum* (dispersed in PG) | 1% of *Hypericum* | Medium | Low | High | High | Yellow Fragrance release |
| Calcium alginate | 1 | Low | Low | Medium | Medium | Grain |
| Aluminum chlorohydrate | 1 | Low | Low | Low | Medium | |
| *Aniba Rosaedora* | 1 | Medium | High | Medium | Medium | Fragrance release |
| *Cinnamomum Cassia* | 1 | Medium | Medium | Medium | Medium | Fragrance release |
| *Eucalyptus Radiata* | 1 | Low | Low | Low | Medium | Fragrance release |
| *Mentha piperita* | 1 | High | High | High | Medium | Fragrance release |
| *Cynopogon Martini* | 1 | Medium | High | Medium | Medium | Fragrance release |
| Lidocaine (dispersed in ethanol) | 1% of lidocaine | Low | High | High | High | |
| Benzocaine (dispersed in ethanol) | 1% of benzocaine | High | High | High | Medium | |
| Ethanol | 2 | Low | High | Low | High | |
| Ethanol | 4 | Low | High | Low | Medium | |
| NaCl | 1 | Low | Low | High | High | Grain |

TABLE 5-continued

| Ingredient | Ingredient wt. % in XX-5501 #19809-129B | Shine | Smoothness | Transparency through the film | Ability to read a text though the film | Comment |
|---|---|---|---|---|---|---|
| Castor oil | 1 | Medium | High | High | High | |
| Castor oil | 2 | Low | Medium | Medium | medium | |

Example 7

Preparation Procedure:
a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.
b. A film of wet saccharide-siloxane containing the ingredient is coated on fluorinated liner using lab coating table and 100 µm shims.

Testing Procedure:
a. mechanical properties—A rectangle of 2 cm×5 cm is cut in each film and evaluated for cohesion by stretching the film between fingers.

TABLE 6

| Ingredient | ingredient wt. % in XX-5501 #19809-129B | Removability from fluorinated film | Elastic Modulus | Resistance to break | Elongation |
|---|---|---|---|---|---|
| XX-5501 #19809-129B | 0 | Medium | Medium | Low | Low |
| *Arnica montana* tincture | 1 | Medium | High | High | Low |
| *Centella Asiatica* (dispersed in PG) | 1% of *Centella* | Low | Low | Low | Low |
| Propylene glycol | 10 | Low | Low | Low | Low |
| Propylene glycol | 1 | Low | Medium | Low | High |
| *Hypericum Perforatum* (dispersed in PG) | 1% of *Hypericum* | Medium | Medium | Low | High |
| Calcium alginate | 1 | High | High | High | Low |
| Aluminum chlorohydrate | 1 | High | Medium | Medium | Low |
| *Aniba Rosaedora* | 1 | High | Medium | Medium | Low |
| *Cinnamomum Cassia* | 1 | High | High | High | Low |
| *Eucalyptus Radiata* | 1 | High | High | High | Low |
| *Mentha piperita* | 1 | High | High | High | Low |
| Cynopogon Martini | 1 | Medium | Medium | Medium | Low |
| Lidocaine (dispersed in ethanol) | 1% of lidocaine | Low | Low | Low | Medium |
| Benzocaine (dispersed in ethanol) | 1% of benzocaine | Low | Medium | Medium | High |
| Ethanol | 2 | Medium | Medium | Low | Medium |
| Ethanol | 4 | Low | Medium | Low | Low |
| NaCl | 1 | High | Low | Low | Medium |
| Castor oil | 1 | Medium | Medium | Medium | Low |
| Castor oil | 2 | Medium | Medium | Medium | Low |

Example 8

Preparation Procedure:
a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.
b. Preparation procedure: a film of wet saccharide-siloxane containing the ingredient is coated on fluorinated liner using lab coating table and 100 µm shims.

Testing Procedure:
a. Film appearance—The film is observed visually for shine, transparency through the film, transparency on a paper (could we read a text through the film when the film is on a book), general appearance smooth or rough.

TABLE 7

| Ingredient | Ingredient wt. % in XX-5501 #19809-129A | Shine | Smoothness | Transparency through the film | Ability to read a text though the film |
|---|---|---|---|---|---|
| XX-5501 #19809-129A | 0 | High | High | Medium | High |
| FA 4002 ID | 1 | Medium | Medium | Medium | Medium |
| FA 4002 ID | 10 | Low | Medium | Low | Medium |
| FA 4001 CM | 1 | Medium | Medium | High | High |

TABLE 7-continued

| Ingredient | Ingredient wt. % in XX-5501 #19809-129A | Shine | Smoothness | Transparency through the film | Ability to read a text though the film |
|---|---|---|---|---|---|
| FA 4001 CM | 10 | Low | Low | Medium | High |
| 193 Fluid | 1 | Medium | Low | Low | Low |
| 193 Fluid | 5 | Low | Low | Medium | Medium |
| Glycerin | 1 | Low | Low | Low | Medium |
| Glycerin | 5 | Low | Low | Low | Medium |

Example 9

Preparation Procedure:
  a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.
  b. Preparation procedure: a film of wet saccharide-siloxane containing the ingredient is coated on fluorinated liner using lab coating table and 100 µm shims.

Testing Procedure:
  a. Film appearance—The film is observed visually for shine, transparency through the film, transparency on a paper (could we read a text through the film when the film is on a book), general appearance smooth or rough.

TABLE 8

| Ingredient | Ingredient wt. % in XX-5501 #19809-129B | Shine | Smoothness | Transparency through the film | Ability to read a text though the film |
|---|---|---|---|---|---|
| XX-5501 #19809-129B | 0 | High | High | Medium | High |
| FA 4002 ID | 1 | Medium | Medium | Medium | Medium |
| FA 4002 ID | 10 | Low | Medium | Medium | Medium |
| FA 4001 CM | 1 | Medium | Low | Low | High |
| FA 4001 CM | 10 | Low | Low | Low | Medium |
| 193 Fluid | 1 | High | Low | Medium | Medium |
| 193 Fluid | 5 | Low | Medium | Low | Medium |
| Glycerin | 1 | Medium | Medium | Low | Medium |
| Glycerin | 5 | Low | High | Low | Low |

Example 10

Preparation Procedure:
  a. The saccharide-siloxane solution and the active or inactive ingredient are weighed and mixed on a Hauschild Speedmixer™ centrifugal mixer (Flacktek, Inc. Landrum, S.C.) for 20 s at 2000 rpm.
  b. Preparation procedure: a film of wet saccharide-siloxane containing the ingredient is coated on fluorinated liner using lab coating table and 100 µm shims.

Testing Procedure:
  a. actives were released in a good solvent (water) after 8 hours of digestion at 32° C. (skin temperature) in pressurized bombs (Parr digestion system). After extraction, aqueous solutions were analyzed by WDXKF in order to quantify the amounts of actives released from wound care films.

TABLE 9

| Samples | NaCl % extracted | AlCl3 % extracted |
|---|---|---|
| XX-5501 #19786-93 | 0 | 0 |
| XX-5501 #19786-93 + 2.4% NaCl | 0 | — |
| XX-5501 #19786-93 + 12% NaCl | 2 | — |

TABLE 9-continued

| Samples | NaCl % extracted | AlCl3 % extracted |
|---|---|---|
| XX-5501 #19786-93 + 24% NaCl | 4 | — |
| XX-5501 #19786-93 + 2.4% AlCl3 | — | 50 |
| XX-5501 #19786-93 + 12% AlCl3 | — | 14 |
| XX-5501 #19786-93 + 24% AlCl3 | — | 10 |

Example 11

This example illustrates the effect of Cab-O-Sil treated and untreated silicas in the formulation, on viscosity.

The saccharide siloxane composition XX-5501 is prepared according to the following procedure: 52.5 g of GL-8211 saccharide-siloxane as prepared in Example 1 is diluted with a 90/10 by weight solution of 0.65 cSt 200 Fluid (Dow Corning Corp, Midland Mich.) and 200 proof ethanol until a 50% copolymer concentration is achieved. The dilution is accomplished by sequential additions of the solvent followed by mixing on a Hauschild Speedmixer™ centrifugal mixer (Flacktek, Inc. Landrum, S.C.) until homogenous. The crosslinker is a 10% by weight solution of phenyl boronic acid (Sigma-Aldrich Co., St. Louis, Mo.) in 200 proof ethanol. 3.94 g of this crosslinker solution and 4.73 g silica is added to the formulation. The saccharide-siloxane solution, silica, and crosslinker solutions are mixed on a Hauschild Speedmixer™ centrifugal mixer (Flacktek, Inc. Landrum, S.C.) until homogenous. At the end 90/10 hexamethyldisiloxane/ethanol solvent mixture is added to achieve 35% solid saccharide-siloxane concentration in the final formulation.

Cab-O-Sil TS-530 is a hexamethyldisilazane treated silica and Cab-O-Sil PTG is an untreated fumed silica (Cabot Co. Boston, Mass.).

Table 10 summarizes the viscosity measurements of the formulations prepared with treated and untreated Cab-O-Sil® silicas over 3 months testing period.

TABLE 10

| Silica Type | crosslinker level (pts) | Viscosity after prep. (cps) | Viscosity 1 month (cps) | Viscosity 2 month (cps) | Viscosity 3 month (cps) |
|---|---|---|---|---|---|
| Cab-O-Sil TS-530 | 1.5 | 1,200 | 2,200 | 25,600 | 70,000 |
| Cab-O-Sil PTG | 1.5 | 2,720 | 1,900 | 1,600 | 1,360 |

The data demonstrates that the viscosity of the untreated silica formulation is slightly decreased, while the viscosity of the treated silica formulation is increased largely over the testing period.

The samples were evaluated on surface, also. The friction and dirt resistance of the untreated silica containing films were enhanced.

Example 12

This example illustrates the effect on the physical characteristics of the film from varying the crosslinker concentration. Samples are prepared as in Example 11, above, except that the crosslinker concentration is altered between 0.1-2.0 pts calculated to the siloxane content.

Film samples were drawn from the formulations having various crosslinker concentrations. The appearance of the film samples at and under 1.5 pts were smooth without any bubbles, which were observed at higher crosslinker concentrations.

The physical characteristic data set forth in Table 11 demonstrates the dependence of the tensile strength and elongation of the sugar siloxane film formers on the crosslinker concentration.

TABLE 11

| Crosslinker Concentration (pts) | Tensile Strength (psi) | Elongation (%) | Toughness (lbf/in$^2$) | 50% Modulus (psi) | 100% Modulus (psi) |
|---|---|---|---|---|---|
| 0.1 | 80.5 | 99.3* | 68.7 | 81.4 | 85.4 |
| 0.5 | 85.2 | 187.5 | 155.2 | 82.9 | 99.4 |
| 1.0 | 99.5 | 161.6 | 155.2 | 100.2 | 115.9 |
| 1.5 | 151.7 | 132.0 | 168.2 | 140.5 | 163.2 |
| 2.0 | 174.8 | 59.5 | 69.2 | 187.8 | — |

The tensile strength of the 1.5 pts crosslinker film was slightly less, but the elongation value was improved compared to the benchmark formulation. The physical properties of the saccharide siloxane films with lower than 1.5 pts crosslinker concentrations were undesirable.

Example 13

This Example illustrates in-solvent saccharide-siloxane synthesis.

The saccharide siloxane polymer is prepared in 90/10 (w/w) hexamethyldisiloxane (0.65 cSt 200 Fluid, Dow Corning Corp., Midland, Mich.)/200 proof ethanol solvent system according to the following procedure: DC® 2-8211 Polymer is reacted with gluconolactone (1:1 lactone to amine functional group stoichiometry) in MM/EtOH solvent system at 70° C. for 6 hours. GC analysis is used to detect ethanol and hexamethyldisiloxane content in final product.

A "cutback method" is necessary to incorporate the Cab-O-Sil PTG untreated silica (Cabot Co., Boston, Mass.), because of the reduced saccharide siloxane solution viscosity. The cutback method involves alternating small incremental additions of the silica filler and saccharide siloxane solution to the formulation followed by mixing on a Hauschild Speedmixer™ centrifugal mixer (Flacktek, Inc. Landrum, S.C.) until homogeneous formulation achieved. Finally, a 10% solution in ethanol of the phenylboronic acid crosslinker is added and mixed.

Example 14

The data set forth in Table 12 details the properties of two exemplary polymers that were reacted with the saccharide and tested in the film forming formulation. DC® 2-8211 has nominally a functional group per every 53 dimethylsiloxy units compared to DC® 2-8460, which has one functional group per 42 dimethylsiloxy units.

TABLE 12

| Polymer Name | MW | DP | mpc F |
|---|---|---|---|
| 2-8211 | 22932 | 300 | 1.9 |
| Q2-8460 | 31445 | 410 | 2.4 |

The DC® 2-8211-GL and DC® Q2-8460 saccharide siloxane polymers are prepared in 90/10 (w/w) hexamethyldisiloxane (0.65 cSt 200 Fluid, Dow Corning Corp., Midland, Mich.)/200 proof ethanol solvent system according to the following procedure: The amino siloxane polymer is reacted with gluconolactone (1:1 lactone to amine functional group stoichiometry) in MM/EtOH solvent system at 70° C. for 6 hours. GC analysis is used to detect ethanol and hexamethyldisiloxane content in final product.

A cutback method is necessary to incorporate the Cab-O-Sil PTG untreated silica (Cabot Co., Boston, Mass.), because of the reduced saccharide siloxane solution viscosity. This is done by alternating small incremental additions of the silica filler and saccharide siloxane solution to the formulation followed by mixing on a Hauschild Speedmixer™ centrifugal mixer (Flacktek, Inc. Landrum, S.C.) until homogeneous formulation achieved. Finally, a 10% solution in ethanol of the phenylboronic acid crosslinker is added and mixed. 66.34 g of polymer solution in 90/10 (w/w) hexamethyldisiloxane/200 proof ethanol solvent system, 4.73 g of untreated silica and 3.94 g of crosslinker solution are used in each formulation.

Films were drawn from each formulation and physical properties were compared to each other as set forth in Table 13.

TABLE 13

| Silicone Polymer Type | Tensile Strength (psi) | Elongation at break % |
|---|---|---|
| DC ® 8211-GL | 118.9 | 61.68 |
| DC ® Q2-8460-GL | 234.9 | 77.93 |

Notably, the film prepared with the DC® 8460-GL is stronger than the 8211-GL containing matrix. The increased strength may be due to the greater number of reactive sites per polymer in the DC® 2-8460.

Example 15

This Example illustrates drug incorporation and drug release from films according to specific embodiments of the invention and provides two examples of drug-incorporated formulations suitable for drug delivery applications.

Figure 1A:
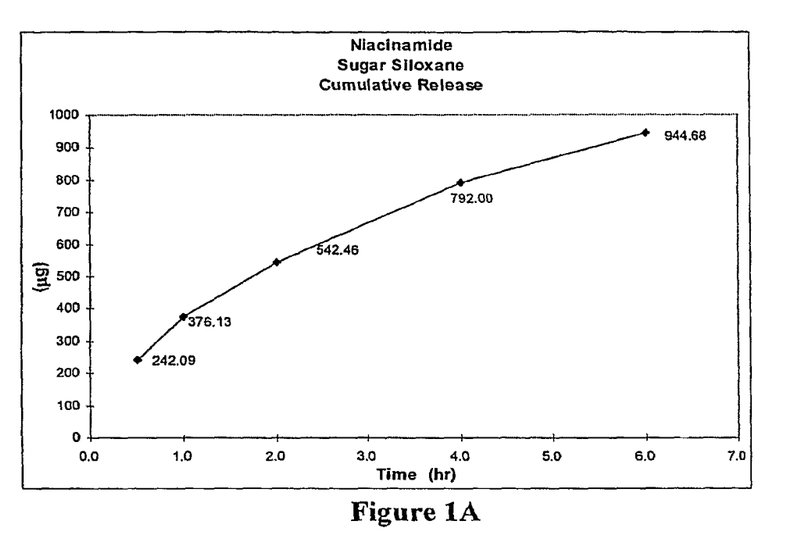
FIG. 1A. sets forth data relating to cumulative release of the drug agent Niacinamide from inventive films.
Figure 1B:
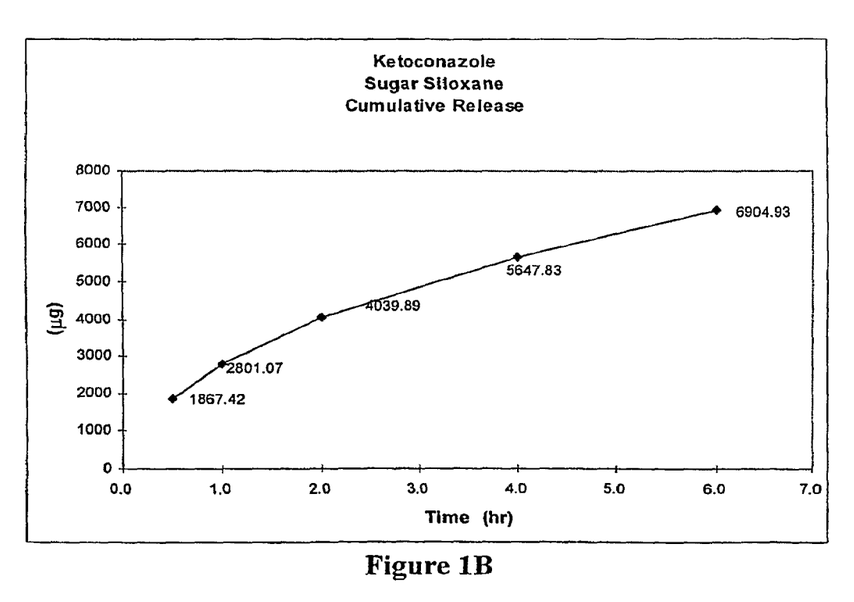
FIG. 1B. sets forth data relating to cumulative release of the drug agent Ketoconazole from inventive films. Determination of active agent release was conducted using Franz static diffusion cells having defined receiving volumes.

The saccharide siloxane polymer is prepared in 90/10 (w/w) hexamethyldisiloxane (0.65 cSt 200 Fluid, Dow Corning Corp., Midland, Mich.)/200 proof ethanol solvent system according to the following procedure: DC® 2-8211 Polymer is reacted with gluconolactone (1:1 lactone to amine functional group stoichiometry) in MM/EtOH solvent system at 70° C. for 6 hours. GC analysis is used to detect ethanol and hexamethyldisiloxane content in final product. Once again, a cutback method, as described above, is necessary to incorporate the Cab-O-Sil PTG untreated silica. Finally, a 10% solution in ethanol of the phenylboronic acid crosslinker is added and mixed. 17.69 g of polymer solution in 90/10 (w/w) hexamethyldisiloxane/200 proof ethanol solvent system, 0.2 g of an exemplary drug agent, 1.06 g of untreated silica and 1.05 g of crosslinker solution are used in each formulation. Two active drugs, Niacinamide and Ketoconazole, respectively, were incorporated into drug delivery films employing this protocol. Determination of active agent release was conducted using Franz static diffusion cells having defined receiving volumes. Data are set forth graphically in FIGS. 1A and B.

The invention claimed is:

1. A cross-linkable therapeutic film composition comprising:
   a) a saccharide-siloxane copolymer;
   b) a crosslinking agent;
   c) about 0.1 to about 70 wt % of one or more active/inactive ingredients; and
   d) at least one of a solvent and solvent mixture,
   wherein the saccharide-siloxane copolymer has the following formula:

$R^2{}_a R^1{}_{(3-a)}SiO—[(SiR^2R^1O)_m—(SiR^1{}_2O)_n]_y—SiR^1{}_{(3-a)}R^2{}_a$ wherein $R^1$ can be the same or different and comprises hydrogen, $C_1$-$C_{12}$ alkyl, an organic radical, or $R^3$—Q,
   Q comprises an epoxy, cycloepoxy, primary or secondary amino, ethylenediamine, carboxy, halogen, vinyl, allyl, anhydride, or mercapto functionality,
   m and n are integers between 0 and 10,000 and may be the same or different,
   each a is independently 0, 1, 2, or 3,
   y is an integer such that the copolymer has a molecular weight less than 1 million,
   $R^1{}_{(3-a)}SiO—[(SiR^2R^1O)_m—(SiR^1{}_2O)_n]_y—SiR^1{}_{(3-a)}$ is an organosiloxane polymer component,
   $R_2$ has the formula $Z—(G^1)_b$-$(G^2)_c$, and there is at least one $R^2$ per copolymer,
   wherein $G^1$ is a saccharide component comprising 5 to 12 carbons,
   b+c is 1-10, b or c can be 0, either b or c must be 1,
   $G^2$ is a saccharide component comprising 5 to 12 carbons additionally substituted with organic or organosilicon radicals,
   Z is a linking group between the organosiloxane polymer component and the saccharide component and is independently selected from the group consisting of:
   —$R^3$—NHC(O)—$R^4$—;
   —$R^3$—NHC(O)O—$R^4$—;
   —$R^3$—NH—C(O)—NH—$R^4$—;
   —$R^3$—C(O)—O—$R^4$—;
   —$R^3$—O—$R^4$—;
   —$R^3$—S—$R^4$—;
   —$R^3$—CH(OH)—$CH_2$—O—$R^4$—;
   —$R^3$—CH(OH)—$CH_2$—NH—$R^4$—; and
   —$R^3$—N($R^1$)—$R^4$, and $R^3$ and $R^4$ are divalent spacer groups comprising $(R^5)_r$, $(R^6)_s (R^7)_t$,
   where at least one of r, s and t must be 1,
   $R^5$ and $R^7$ are either $C_1$-$C_{12}$ alkylene or $((C_1$-$C_{12})O)_p$ where p is any integer 1-50 and each $(C_1$-$C_{12})O$ may be the same or different, and
   $R^6$ is —N($R^8$)—, where $R^8$ is H or $C_1$-$C_{12}$ alkyl or is Z—X, wherein Z is previously defined or $R^3$,
   wherein the film composition has therapeutic properties, the film composition having a thickness of up to 500 microns.

2. The film composition of claim 1 wherein the saccharide siloxane copolymer comprises a hydroxyl functionality of at least three.

3. The film composition of claim 1 wherein the at least one Polyhydroxyl-functional saccharide comprises an aldonic acid or an oligoaldonic acid.

4. The film composition of claim 3 wherein the aldonic acid or the oligoaldonic acid comprises a lactone.

5. The film composition of claim 4 wherein the lactone comprises gluconolactone or lactobionolactone.

6. The film composition of claim 1 wherein the linking group comprises an amide, an amino, a urethane, a urea, an ester, an ether, a thioether, or an acetal linking group.

7. The film composition of claim 1, wherein the at least one Polyhydroxyl-functional saccharide comprises gluconolactone and the functionalized organosiloxane polymer comprises a polydimethylsiloxane having pendant minoethylaminoisobutyl groups.

8. The film composition of claim 1, further comprising one or more additional saccharide-siloxane copolymers and suitable cross linkers to form a blended film-forming composition.

9. The film composition of claim 1 further delivered onto a biological substrate and forming a cohesive and substantive film.

10. The film composition of claim 9, wherein the one or more active or/and inactive ingredients is selected from the following: a catalyst; a filler; a pigment; a UV stabilizer; a fragrance; an essential oil; a thermal stabilizer; a rheology modifier; a thickener; an adhesion promoter; a biocide; an antifungal; an antibiotic; a preservative; an enzyme; a peptide; a pressure sensitive adhesive; a surface-active agent; a pharmaceutical active; a cosmetic ingredient; a resin; and an aqueous ingredient.

11. The film composition of claim 10 wherein the biological substrate comprises human skin or nail.

12. The film composition of claim 11 wherein the is incorporated into a wound dressing, a bandage, a transdermal drug delivery patch, a topical drug delivery formulation, a cosmetic composition or a fragrance delivery patch.

13. The film composition of claim 1, wherein the active ingredient comprises a medicament or pharmaceutical agent and the composition is incorporated into a transdermal drug delivery patch.

14. The film composition of claim 1, wherein the active ingredient comprises at least one biocide.

15. A method for delivering at least one active agent topically to, or transdermally through a biological substrate, the method comprising: wet application of the cross-linkable therapeutic film composition according to claim 1 to a biological substrate, and curing the composition to form a film directly on the biological substrate.

* * * * *